(12) United States Patent
Kato et al.

(10) Patent No.: US 9,989,513 B2
(45) Date of Patent: Jun. 5, 2018

(54) OIL CONTENT MEASUREMENT DEVICE

(71) Applicant: HITACHI, LTD., Tokyo (JP)

(72) Inventors: Hajime Kato, Tokyo (JP); Shigeki Terui, Tokyo (JP); Minoru Morita, Tokyo (JP); Yoshio Nakayama, Tokyo (JP); Makoto Onishi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 191 days.

(21) Appl. No.: 15/188,206

(22) Filed: Jun. 21, 2016

(65) Prior Publication Data
US 2017/0030885 A1    Feb. 2, 2017

(30) Foreign Application Priority Data
Jul. 28, 2015   (JP) .................................. 2015-148290

(51) Int. Cl.
| | | |
|---|---|---|
| G01N 33/20 | (2006.01) | |
| G01N 33/28 | (2006.01) | |
| G01N 29/02 | (2006.01) | |
| G01N 29/036 | (2006.01) | |
| G01N 29/22 | (2006.01) | |

(52) U.S. Cl.
CPC ....... *G01N 33/2847* (2013.01); *G01N 29/022* (2013.01); *G01N 29/036* (2013.01); *G01N 29/222* (2013.01); *G01N 2291/014* (2013.01); *G01N 2291/0226* (2013.01); *G01N 2291/0256* (2013.01); *G01N 2291/0426* (2013.01)

(58) Field of Classification Search
CPC ........ G01F 23/00; G01F 23/26; G01F 23/284; G01F 23/2962; G01F 23/0076; G01N 33/2847; G01N 29/02

USPC ....................... 73/61.45, 152.08, 291, 290 R
See application file for complete search history.

(56) References Cited

U.S. PATENT DOCUMENTS

| | | | |
|---|---|---|---|
| 3,695,108 A * | 10/1972 | Wygant | G01F 23/26 |
| | | | 73/290 R |
| 8,841,926 B2 * | 9/2014 | Fuetterer | B41J 2/17509 |
| | | | 324/671 |
| 9,052,065 B2 * | 6/2015 | Mackey | F17C 7/02 |
| 2009/0157345 A1 * | 6/2009 | Yoshioka | G01N 27/221 |
| | | | 702/136 |

(Continued)

FOREIGN PATENT DOCUMENTS

JP            2013-024562 A    2/2013

*Primary Examiner* — Eric S McCall
*Assistant Examiner* — Mohammed E Keramet-Amircola
(74) *Attorney, Agent, or Firm* — Oliff PLC

(57) ABSTRACT

An oil content measurement device includes a fluid device which mixes water to be treated containing oil content with a solvent and extracts the oil content into the solvent, a sensor unit which has a casing storing a quartz crystal oscillator therein with a ring-like spacer in between, a dispensing nozzle which is disposed above the oscillator at a predetermined gap there between and feeds a predetermined amount of the solvent after the oil content has been extracted on the oscillator, a sensor circuit which measures a resonance frequency of the oscillator, and controller which controls at least the fluid device and the sensor circuit. Provided is a arithmetic logical unit, based on a change amount of the received resonance frequency of the oscillator in the sensor unit to which the solvent after the oil content has been extracted has been fed, measures the oil content remaining on the oscillator.

16 Claims, 11 Drawing Sheets

(56) References Cited

U.S. PATENT DOCUMENTS

| | | | |
|---|---|---|---|
| 2009/0211984 A1* | 8/2009 | Petty | C02F 1/42 |
| | | | 210/741 |
| 2011/0174709 A1* | 7/2011 | Mori | C02F 3/12 |
| | | | 210/202 |
| 2014/0083694 A1* | 3/2014 | Scott | F22B 37/26 |
| | | | 166/272.3 |
| 2014/0238114 A1* | 8/2014 | Klasner | G01N 29/022 |
| | | | 73/61.75 |

* cited by examiner

… (1) …

OIL CONTENT MEASUREMENT DEVICE

CLAIM OF PRIORITY

The present application claims priority from Japanese Patent application serial No. 2015-148290, filed on Jul. 28, 2015, the content of which is hereby incorporated by reference into this application.

FIELD OF THE INVENTION

The present invention relates to an oil content measurement device which measures water quality of water to be treated at a water treatment site, in particular oil content remaining in, for example, produced water or waste water, that is, the remaining oil content.

BACKGROUND OF THE INVENTION

As one measuring the oil content, a technology described in Patent Document 1 is known. In Patent Document 1, a quartz crystal microbalance (hereinafter referred to as QCM) is used, droplets of water soluble ink which is a measuring object are dropped onto a quartz crystal oscillator by an ink jet, by the change amount of the resonance frequency (fundamental frequency) of the quartz crystal oscillator before dropping the droplets and the resonance frequency measured after dropping the droplets, the mass of the deposit that is the water soluble ink on the quartz crystal oscillator is measured. In other words, using the characteristics of the change of the resonance frequency (called also as natural frequency) and the deposit amount on the surface thereof, the oil content in the sample water of a minute amount is measured.

CITATION LIST

Patent Document

Patent Document 1: Japanese Patent Application Laid-open No. 2013-24562

However, in the configuration of Patent Document 1, the water soluble ink which is a measuring object is directly made to fall in droplets onto the quartz crystal oscillator to measure the mass of the oil content in the water soluble ink, and one in which the oil content which is the ink component is contained by a large amount is made the measuring objects in the first place.

Therefore, for example, with respect to measurement of a minute amount of the oil content contained in produced water containing very minute amount of oil content in an Oil & Gas site, domestic wastewater, or industrial wastewater, consideration is not paid at all. Namely, it is difficult to apply the configuration of Patent Document 1 to measurement of the oil content contained in water to be treated stipulated by an official law (Water Pollution Control Law).

SUMMARY OF THE INVENTION

Thus, the present invention provides an oil content measurement device capable of accurately measuring the oil content remaining in water to be treated in a water treatment site even in a case where the oil content remaining in water to be treated is dilute.

In order to solve the problem described above, an oil content measurement device of an aspect of the present invention comprises: a fluid device which mixes water to be treated containing oil content with solvent and extracts the oil content into the solvent; a sensor unit which includes a casing storing a quartz crystal oscillator therein with a ring-like spacer in between; a dispensing nozzle connected to the fluid device, being disposed above the quartz crystal oscillator of the sensor unit at a predetermined gap therebetween, which feeds a predetermined amount of the solvent after the oil content has been extracted thereinto onto the quartz crystal oscillator; a sensor circuit which measures a resonance frequency of the quartz crystal oscillator at a predetermined period; a controller which controls at least the fluid device and the sensor circuit; and an arithmetic logical unit which receives resonance frequency of the quartz crystal oscillator in the sensor unit to which the predetermined amount of the solvent after the oil content has been extracted thereinto has been fed by the dispensing nozzle form the sensor circuit, and measures the oil content remaining on the quartz crystal oscillator after the solvent has evaporated based on a change amount of the received resonance frequency.

According to the present invention, an oil content measurement device can be provided which is capable of accurately measuring the oil content remaining in water to be treated in a water treatment site for, for example, Oil & Gas and the like even in a case where the oil content remaining in water to be treated is dilute.

Problems, configuration, and effects other than those described above will be more clarified by a description of an embodiment below.

DETAILED DESCRIPTION OF THE PREFERRED EMBODIMENTS

Figure 1:
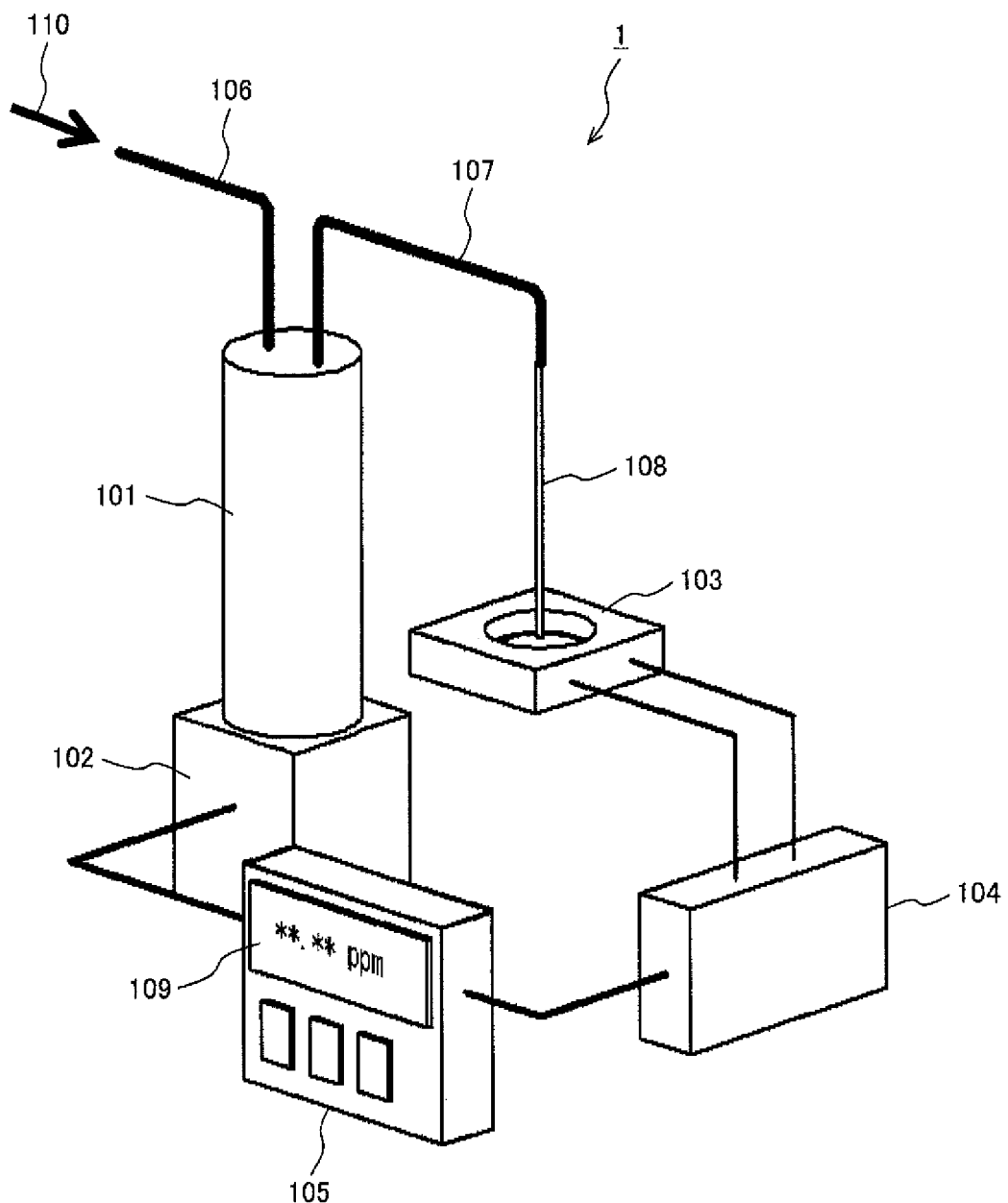
FIG. 1 is an overall configuration diagram of an oil content measurement device in relation with an embodiment of the present invention.

The water to be treated in the present specification includes: for example, produced water at an Oil & Gas site, domestic wastewater, or industrial wastewater and the like, and is possibly called sample water as the case may be. Further, although the measured value by QCM method is referred to below as the resonance frequency, the natural frequency also has the same meaning.

First, the oil content analysis of the water to be treated is stipulated by an official law (Water Pollution Control Law), in this analysis method, and a substance extracted into n-hexane (hereinafter referred to merely as "hexane") is defined as oil content in the water to be treated. Therefore, in the official law, first, the oil content is entirely extracted from the water to be treated into the hexane as a solvent, and then based on mass of a substance remaining after evaporating this hexane, concentration of the oil content of the original water to be treated is measured.

Although an electronic force balance and the like of high-accuracy and highly sensitivity is used for measuring the mass, when the water to be treated of a diluted concentration is to be measured, the sufficient oil content to be detectable even by an electronic force balance should be extracted into the hexane, and therefore much volume of both of the water to be treated and the hexane are necessary. Accordingly, a high temperature and reduced pressure environment are required in order to evaporate the much volume of hexane in shorter time which is not suitable to quick in-situ analysis required in a water treatment site for Oil & Gas and the like.

As an analysis method substituted for the official law, devices applying the spectroscopic analysis have been put into practical use, and a handy type one usable even outdoors has also been commercialized. However, it is necessary to perform the preliminary treatment of the sample such as a removing treatment of a solid matter, extraction of solvent and so on beforehand, and it is required to work out a calibration curve between the concentration and absorbance for each analysis object by using the control sample and the like.

As described above, in any of the solvent extraction method, a gravimetric method, spectroscopic measurement and the like based on the official law, it has been impossible so far to analyze oil content in a water treatment site with sufficient accuracy.

In an oil content measurement device which measures oil content in water to be treated water in relation to an embodiment of the present invention, based on the official law, first, all of the oil content in the water to be treated is moved into the hexane (hexane extraction). Then a predetermined amount of this hexane is supplied to a sensor unit including a quartz crystal oscillator to be described later on, and only the hexane is evaporated. The mass of a substance remained and deposited onto the quartz crystal oscillator after evaporation of hexane (hexane extraction substance (oil content)) is measured based on the change amount of the resonance frequency of the quartz crystal oscillator. Further, based on the measured mass of the hexane extraction substance, the predetermined amount of hexane supplied, and the volumetric amount of the original water to be treated, the concentration of the oil content contained in the water to be treated is measured.

Such a series of analysis processes, that is, the extraction of the oil content into the hexane, the evaporation of the hexane containing the oil content on the quartz crystal oscillator in the sensor unit, the measurement of the mass of the remaining deposit on the quartz crystal oscillator are achieved by a simple device configuration.

Also, the measurement method of obtaining the deposit amount (mass) on the surface of the quartz crystal oscillator based on such change amount of the resonance frequency of the quartz crystal oscillator is called a QCM method, and is put to practical use in a film thickness monitor and the like in a thin film forming process. A commercialized quartz crystal oscillator for QCM has, for example, a diameter of 2 mm to 10 mm, a thickness of several hundreds of micrometers, and a resonance frequency in a band of several megahertz. The mass of the deposit substance on the surface can be measured in the range between several nanograms to several tens of micrograms in order.

The oil content measurement device which measures oil content in water to be treated in relation with the embodiment of the present invention can be applied to a water treatment plant as a remaining oil content monitor of a water/oil separation treatment process and the like of coagulation magnetic separation and the like, and can also be applied to monitoring of the operational status and the performance of the plant.

Hereinafter, the embodiment of the present invention will be described with reference to the drawings.

First Embodiment

FIG. 1 shows an overall configuration diagram of the oil content measurement device in relation with an embodiment of the present invention. The oil content measurement device 1 of the present embodiment includes a fluid device 101 of a syringe type for extracting oil content in water to be treated into hexane as a solvent and also delivering the extracted oil content, a motor 102 for driving a piston in the fluid device 101, a sensor unit 103 as a QCM sensor which evaporates the hexane into which the oil content has been extracted and further measures mass of the remaining substance (oil content) extracted into the hexane, a sensor circuit 104 for oscillating a quartz crystal oscillator provided inside of the sensor unit 103 and measuring a resonance frequency, and a controller 105 including a display section 109 that displays the measurement results and controlling the entire oil content measurement device 1.

Further, an electric power supply for driving these devices is also provided although it is not shown. Especially, when it is used outdoors where is a water treatment site for Oil & Gas and the like, it is preferable to use a rechargeable battery.

In the fluid device 101, the water to be treated and the hexane 110 as a solvent are sucked through a flow-in pipe 106, and the piston thereinside is driven by the motor 102 to extract oil content in the water to be treated into the hexane (the detail will be described later on). Then after having extracted the oil content in the water to be treated into hexane almost completely, a predetermined amount of the hexane which contains the extracted oil content is supplied to the sensor unit 103 from a dispensing nozzle 108 through a flow-out pipe 107.

Figure 2:
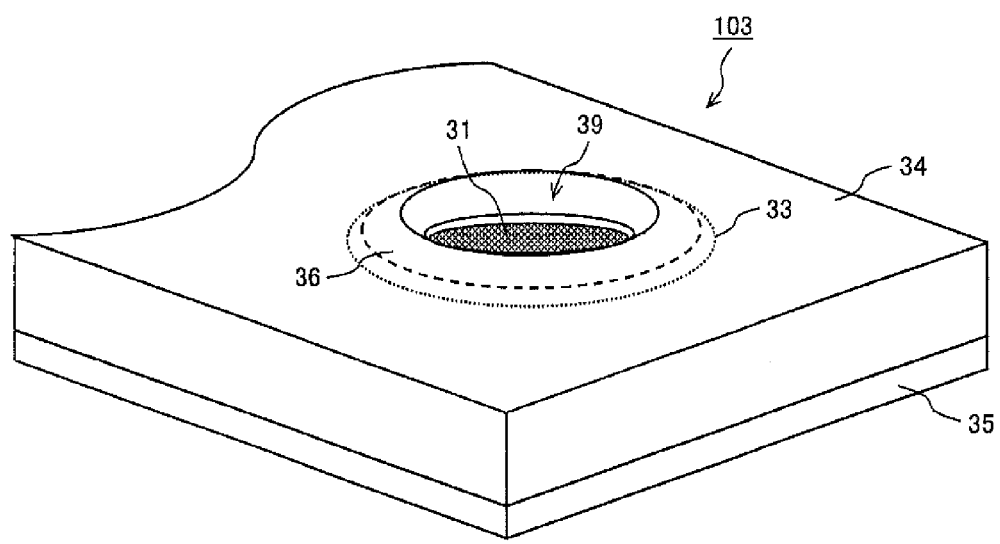
FIG. 2 is a partially translucent perspective view of a sensor unit configuring the oil content measurement device shown in FIG. 1.
Figure 3:
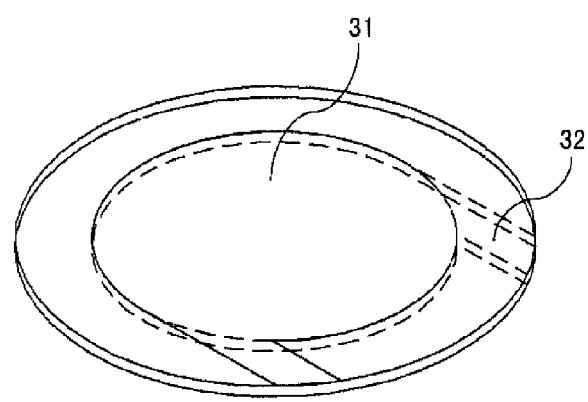
FIG. 3 is a schematic configuration diagram of a quartz crystal oscillator configuring the sensor unit shown in FIG. 2.
Figure 4:
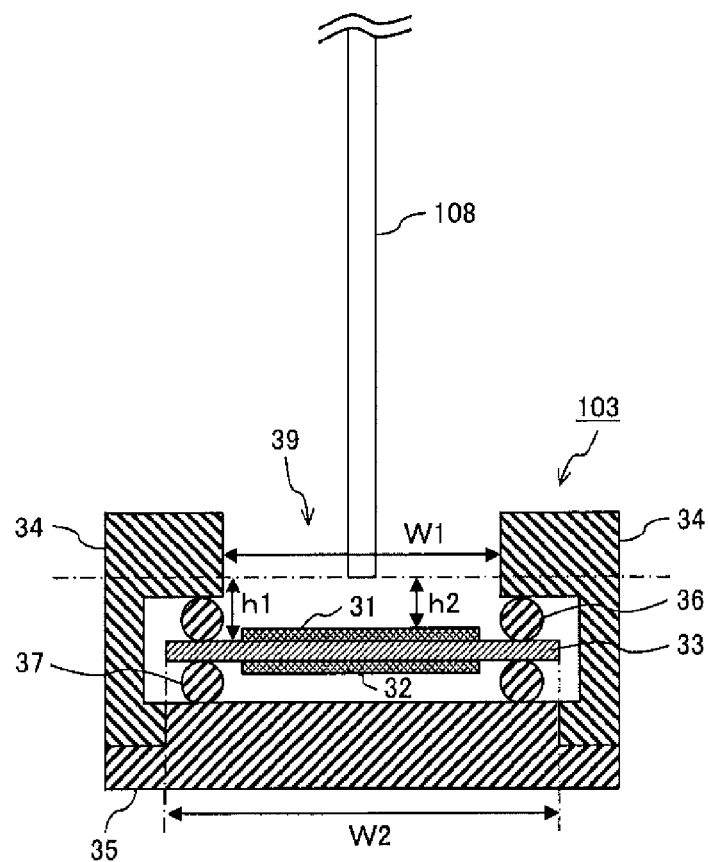
FIG. 4 is a longitudinal sectional view of the sensor unit shown in FIG. 2.

Next, the internal structure and assembly processes of the sensor unit 103 will be described with reference to FIGS. 2 through 8. FIG. 2 is a partially translucent perspective view of the sensor unit 103 shown in FIG. 1, and FIG. 3 is a schematic configuration diagram of the quartz crystal oscillator configuring the sensor unit shown in FIG. 2. FIG. 4 is a longitudinal sectional view of the sensor unit 103 shown in FIG. 2, and FIGS. 5 through 8 are diagrams showing the processes of assembling the sensor unit 103 shown in FIG. 4.

As shown in FIG. 2, the sensor unit 103 as the QCM sensor has a housing composed of an upper casing 34 and a lower casing 35, and includes, on a top surface of the upper casing 34, an opening section 39 penetrating through the upper casing 34. Located immediately below the opening section 39, on a top surface of a quartz crystal oscillator 33 of a disc-like shape (disposed in the housing) shown by a broken line, is a surface electrode 31, for example, formed through a thin-film forming process. Moreover, an upper O ring 36 as a ring-like spacer (disposed in the housing) shown by a broken line abuts a wall surface of the upper casing 34 defining the opening section 39, namely, a back surface of the upper casing 34 outside of the opening section 39, and the top surface of the quartz crystal oscillator 33, and achieves sealing so as to avoid outflow of the supplied hexane after the oil content extraction. Here, the upper O ring 36 as the ring-like spacer is formed of an elastic member such as rubber and the like.

In the QCM method, thickness-shear-direction electrical-mechanical resonator of the quartz crystal oscillator 33 is used, and thus, on both surfaces of a crystal plate cut out in orientation called AT cut, the surface electrode 31 (the side facing the dispensing nozzle 108) and a back electrode 32 (the opposite side of the surface electrode 31 with the crystal plate in between) are provided. These surface electrode 31 and back electrode 32 are formed on the both surfaces of the disc-like crystal plate through a thin-film forming process such as spattering, CVD, or PVD. A film thickness of the formed surface electrode 31 and back electrode 32 is in order of, for example, several nanometers to several micrometers order. In FIG. 3, the back electrode 32 is shown by a broken line since it is located on a back side of the quartz crystal oscillator 33. An oscillation circuit is formed with such a quartz crystal oscillator 33 provided as part of an electric oscillation element, and a resonance frequency upon its oscillation is measured. Used as a material forming these surface electrode 31 and back electrode 32 is, for example, gold (Au), platinum (Pt), or Cr and the like.

In a case where there is a deposit to the electrode surface (surface electrode 31) on one side, oscillation characteristic in the thickness shear-direction changes, and thus its resonance frequency changes (the resonance frequency shifts to the direction of low resonance frequency according to the mass of the deposit). Based on an amount of a decrease in the resonance frequency at this point, the mass of the deposit on the electrode surface is measured. Relationship between the change amount of this resonance frequency and the mass is provided by formula of Sauerbey (hereinafter referred to as formula (1)) with the parameters of the shape of the quartz crystal oscillator 33, the area of the electrode, and the like.

$$\Delta f = -2f_0^2 \times [\Delta m/(A \times (pq \times \mu q)^{1/2})] \quad (1)$$

Here, $\Delta f$ is the change amount of the resonance frequency (Hz), $\Delta m$ is the change amount of the mass (g), $f_0$ is a fundamental resonance frequency (Hz), pq is crystal density (g/cm$^3$), μq is the shear stress of the AT-cut crystal (g/cm·s$^2$), and A is the area of the electrode (cm$^2$), and thus pq=2.648 g/cm$^3$, and μq=2.947×10$^{11}$ g/cm·s$^2$.

In the present embodiment, such a quartz crystal oscillator 33 for the QCM is used as a mass sensor for measuring the mass of oil content in water to be treated.

As shown in FIG. 4, the sensor unit 103 as the QCM sensor unit includes the upper casing 34, the lower casing 35, and the quartz crystal oscillator 33 which is water tightly disposed in an inner space formed by the upper casing 34 and the lower casing 35 with the upper O ring 36 and the lower O ring 37 as the ring-like spacers in between and on which the surface electrode 31 and the back electrode 32 are formed. As shown in FIG. 4, the upper O ring 36 as the ring-like spacer is disposed on the top surface of the quartz crystal oscillator 33 in a manner such as to be slightly separated from the surface electrode 31 towards outer circumference of the surface electrode 31. Similarly, the lower O ring 37 as the ring-like spacer is disposed on a bottom surface of the quartz crystal oscillator 33 in a manner such as to be slightly separated from the back electrode 32 towards outer circumference of the back electrode 32. Therefore, an area of the quartz crystal oscillator 33 and the surface electrode 31 surrounded by the upper O ring 36 can be considered as an area of the surface electrode 31. Hereinafter, an area of a region of the quartz crystal oscillator 33 water-tightly sealed by the upper O ring 36 means the area of the surface electrode 31.

As shown in FIG. 4, the upper casing 34 has both side parts formed into a substantially C shape in vertical section, horizontally extends from an outside to an inside of the both side parts, and has an opening part 39 between mutually facing convex parts of a convex shape in cross section. Specifically, the top surface of the upper casing 34 defines the opening part 39 shaped into a circle from a top view. In contrast, a bottom part of the both side parts of the upper casing 34 horizontally protrudes from the outside to the inside in a similar manner, and has mutually facing convex parts. Namely, the bottom surface of the upper casing 34 defines the opening part shaped into a circle from a bottom view in FIG. 4. The convex part on a top side of the upper casing 34 extends more inwardly than the convex part on its bottom side.

The lower casing 35 has a substantially trapezoidal shape in longitudinal cross section with a step provided at its outer edge part, namely, has therein (excluding an area near the outer edge part) a convex part of a columnar shape protruding upwardly, and a top surface of this convex part is formed flat. The upper casing 34 has an end surface of the convex part, which end surface is provided at the bottom of the upper casing 34 and defines the opening part, and a bottom surface of the convex part respectively abutting against and engaging with an outer circumferential surface and a bottom surface (a top surface of the step part) of the columnar convex part provided at the lower casing 35. Here, the upper casing 34 and the lower casing 35 are formed of, for example, Teflon or a PEEK material having insulation properties and resistance to the solvent.

As shown in FIG. 4, between a width W1 (opening diameter) of the opening part 39 formed at the upper casing 34 and a width (outer diameter) W2 of the flat top surface (a surface abutting against the lower O ring 37 as the ring-like spacer) of the columnar convex part provided at the lower casing 35, relationship W2>W1 is established. Illustrated in FIG. 4 is a case where the outer diameter W2 of the top surface of the columnar convex part provided at the lower casing 35 and an outer diameter of the quartz crystal oscillator 33 are equal, but they are not limited thereto. For example, the outer diameter W2 of the top surface of the columnar convex part described above may be made larger than the outer diameter of the quartz crystal oscillator 33. However, it is preferable that in this case, the outer diameter W2 of the top surface of the columnar convex part provided at the lower casing 35 be at least larger than the outer diameter of the lower O ring 37 as the ring-like spacer. Moreover, a shape of the lower casing 35 is not necessarily limited to a shape having the step part near the outer edge part.

Hereinafter, described in the present embodiment as one example is a case where an outer diameter (diameter) D1 of the circular surface electrode 31 and back electrode 32 is 5.0 mm, an inner diameter D2 of the upper O ring 36 and the lower O ring 37 as the ring-like spacers is 5.5 mm, and an outer diameter D3 of the disk-like quartz crystal oscillator is 8.7 mm. The opening diameter W1 of the opening part 39 is equal to the inner diameter of the upper O ring 36 as the ring-like spacer.

Moreover, as shown in FIG. 4, a vertical distance between a tip part (an end part on a side facing the surface electrode 31) of the dispensing nozzle 108 and the top surface of the quartz crystal oscillator 33, that is, a height h1 from the top surface of the quartz crystal oscillator 33 to the tip part of the dispensing nozzle 108, and a vertical distance between the tip part of the dispensing nozzle 108 and the surface electrode 31, that is, a height h2 from the surface electrode 31 to the tip part of the dispensing nozzle 108 have the following relationship. A thickness of the quartz crystal oscillator 33 including the surface electrode 31 and the back electrode 32 is approximately several hundreds of micrometers, while a film thickness of the surface electrode 31 and the back electrode 32 formed on the front and rear surfaces of the quartz crystal oscillator 33 is several nanometers to several micrometers. Therefore, the vertical distance h2 between the surface electrode 31 and the tip part of the dispensing nozzle 108 is approximated to the vertical distance h1 between the top surface of the quartz crystal oscillator 33 and the tip part of the dispensing nozzle 108.

Assumed is a case where, while the tip part of the dispensing nozzle 108 shown in FIG. 4 is positioned spacer including the opening part 39 with respect to the sensor unit 103, the hexane after the oil content extraction to be described later on is fed from the dispensing nozzle 108 to a region of the quartz crystal oscillator 33 water-tightly sealed at the upper O ring 36 as the ring-like spacer including the opening part 39. At this point, as a result of this supply up to a position where a water surface of the hexane after the oil content extraction reaches the tip part of the dispensing nozzle, the hexane after the oil content extraction to the quartz crystal oscillator 33 is defined by an area of the circular region of the quartz crystal oscillator 33 (the area of the surface electrode 31) water-tightly sealed at the upper O ring 36 and the distance h1 between the tip part of the dispensing nozzle 108 and the quartz crystal oscillator 33. Table 1 shows relationship between the distance h1 between the tip part of the dispensing nozzle 108 and the quartz crystal oscillator 33 and an amount of the fed hexane after the oil content extraction when the outer diameter (diameter) D1 of the surface electrode 31 and the back electrode 32 is 5.0 mm, the inner diameter of the upper O ring 36 and the lower O ring 37 as the ring-like spacers is 5.5 mm, the aperture diameter W1 of the opening part 39 is 5.5 mm, and the outer diameter D3 of the disk-like quartz crystal oscillator 33 is 8.7 mm.

TABLE 1

Relationship between the distance h1 between the tip part of the dispensing nozzle and the quartz crystal oscillator and the amount of the fed hexane after the oil content extraction

| h1 [mm] | Amount of fed hexane after oil content extraction |
|---|---|
| 0.25 mm | 7.1 µL |
| 0.50 mm | 14.2 µL |
| 0.75 mm | 21.3 µL |
| 1.00 mm | 28.4 µL |

As shown in Table 1, the amount of the fed hexane after the oil content extraction which hexane has been fed to the quartz crystal oscillator 33 is 7.1 µL where the distance h1 is 0.25 mm, and the amount of the fed hexane after the oil content extraction which hexane has been fed to the quartz crystal oscillator 33 is 14.2 µL where the distance h1 is 0.50 mm. Moreover, the amount of the fed hexane after the oil content extraction which hexane has been fed to the quartz crystal oscillator 33 is 21.3 µL where the distance h1 is 0.75 mm, and the amount of the fed hexane after the oil content extraction which hexane has been fed to the quartz crystal oscillator 33 is 28.4 µL where the distance h1 is 1.00 mm. The distance h1 between the tip part of the dispensing nozzle 108 and the quartz crystal oscillator 33 is desirably 0.25 mm≤h1≤1.0 mm, and more preferably 0.3 mm≤h1≤0.70 mm. Desirably, the distance h1 between the tip part of the dispensing nozzle 108 and the quartz crystal oscillator 33 is accordingly increased for water to be treated with more dilute oil content.

The distance h1 between the tip part of the dispensing nozzle 108 and the quartz crystal oscillator 33 depends on the inner diameter of the upper O ring 36 as the ring-like spacer and/or the aperture diameter W1 of the opening part 39.

In the present embodiment, as shown in FIG. 4, the opening part 39 is formed into a cylindrical shape penetrating through the upper casing 34, although it is not limited thereto. For example, it may be formed into a shape notched on a horizontal plane located above a top part of cone form by a predetermined distance. Namely, in the longitudinal cross sectional view shown in FIG. 4, an inner circumferential surface of the convex part of the upper casing 34 defining the opening part 39 may be shaped to have an inclined surface inclined outwardly from an inside towards a top. However, in this case, it is desirable that the inclined surface be provided above a position of the tip part of the dispensing nozzle 108 when the dispensing nozzle 108 is positioned with respect to the sensor unit 103.

Next, the processes of assembling the sensor unit 103 will be described. FIGS. 5 through 8 show states in the processes of assembling the sensor unit 103.

Figure 5:
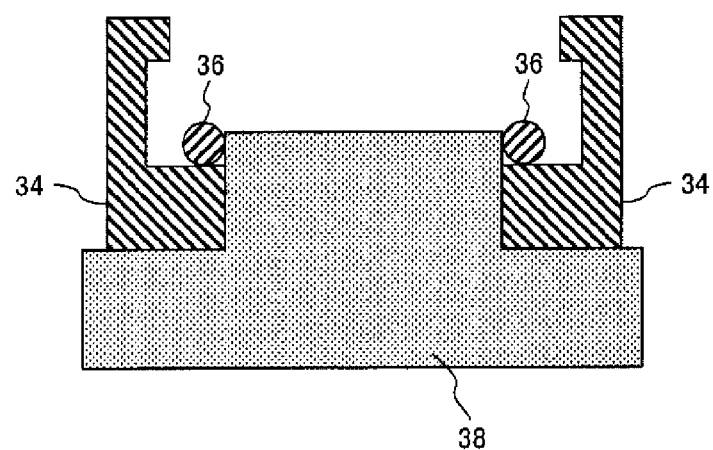
FIG. 5 is a diagram showing a process of assembling the sensor unit shown in FIG. 4.

First, as shown in FIG. 5, a jig 38 having a columnar convex part is prepared. Here, an outer diameter of the columnar convex part of the jig 38 corresponds to the opening diameter W1 of the opening part 39 shown in FIG. 4. From above the jig 38, the upper casing 34 is inserted in a manner such that the opening part 39 defined by the top surface of the upper casing 34 engages with the columnar convex part of the jig 38. Then to an outer circumferential surface of the jig 38, the upper O ring 36 as the ring-like spacer is attached. Upon this attachment, of the top surface (bottom surface in FIG. 4) of the convex part of the upper casing 34 defining the opening part 39, a part abutting against the upper O ring 36 is fixed with, for example, an insulating adhesive agent. This consequently makes it easy to perform, in the next process, operation of installing the quartz crystal oscillator 33 formed with the surface electrode 31 and the back electrode 32. In a case where the outer circumferential surface of the columnar convex part of the jig 38 and an inner circumferential surface of the upper O ring 36 are brought to closely abut each other, the insulating adhesive agent or the like is not necessarily required for the fixation.

Figure 6:
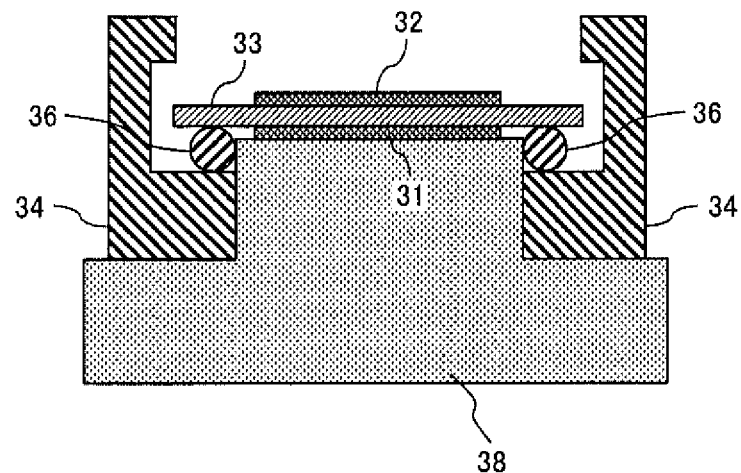
FIG. 6 is a diagram showing a process of assembling the sensor unit shown in FIG. 4.
Figure 7:
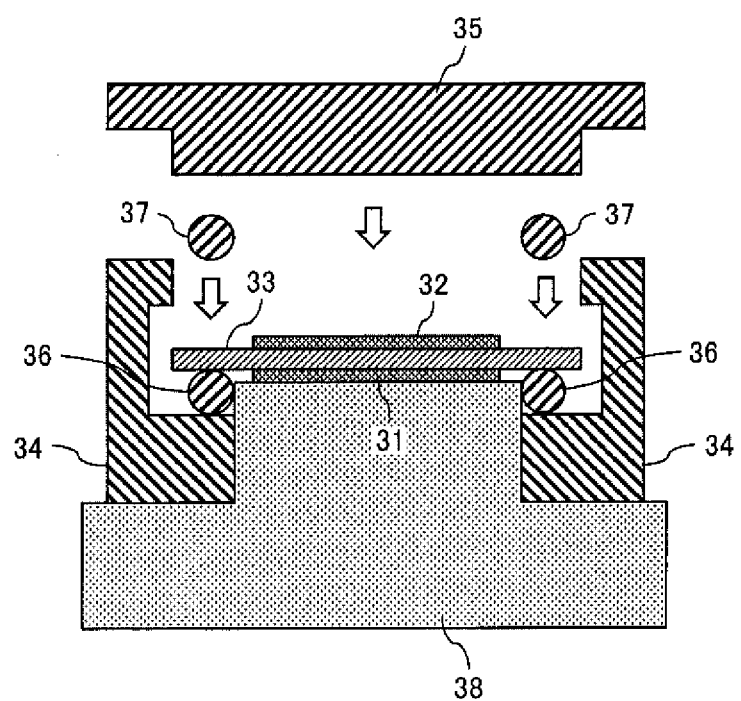
FIG. 7 is a diagram showing a process of assembling the sensor unit shown in FIG. 4.

Subsequently, as shown in FIG. 6, the quartz crystal oscillator 33 formed with the surface electrode 31 and the back electrode 32 is placed from above with the surface electrode 31 is located on a bottom side. At this point, the top surface of the quartz crystal oscillator 33 which is located on an outer circumference side of the surface electrode 31 and which is slightly separated from the surface electrode 31 abuts against the upper O ring 36. Next, as shown in FIG. 7, to a back surface (an upper surface in FIG. 7) of the quartz crystal oscillator 33, the lower O ring 37 is attached. Then the lower casing 35 is disposed in a manner such that a top surface of the columnar convex part provided at the lower casing 35 is located on a bottom side, and is brought into engagement with the upper casing 34 in a manner such as to press the lower O ring 37 from above. At this point, the outer circumferential surface of the columnar convex part provided at the lower casing 35 and the inner circumferential surface of the convex part of the upper casing 34 defining the bottom opening part (FIG. 4) abut each other. Simultaneously therewith, the step part formed around the columnar convex part of the lower casing 35 and the bottom surface of the convex part of the upper casing 34 defining the bottom opening part abut each other.

Figure 8:
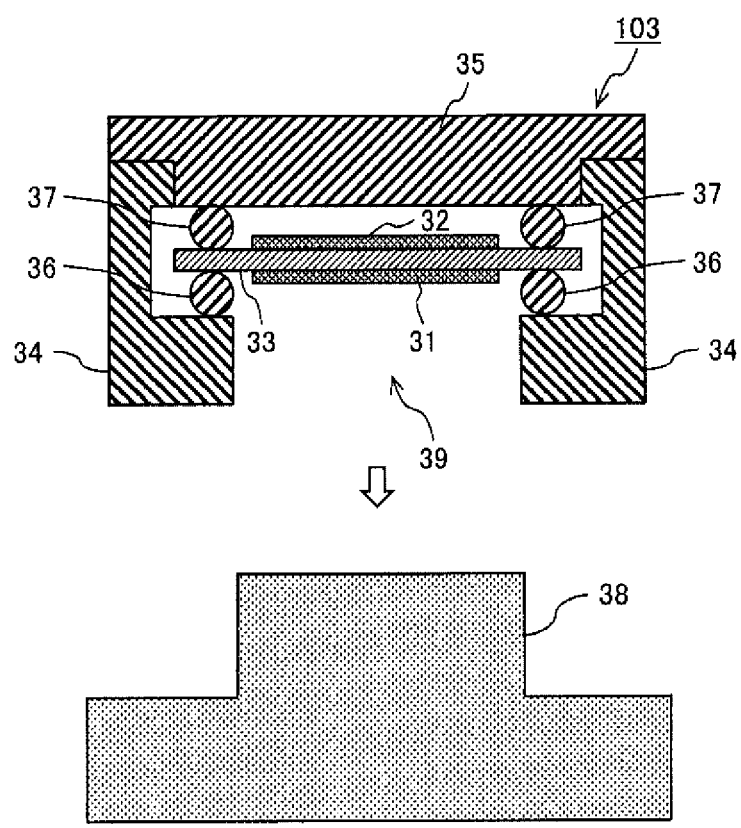
FIG. 8 is a diagram showing a process of assembling the sensor unit shown in FIG. 4.

Next, as shown in FIG. 8, while keeping a state in which the lower O ring 37 is pressed by the flat top surface of the columnar convex part provided at the lower casing 35, the lower casing 35 is screwed with the upper casing 34 by a screw (not shown) or the like. Then the jig 38 is detached, ending the processes of assembling the sensor unit 103.

Figure 9:
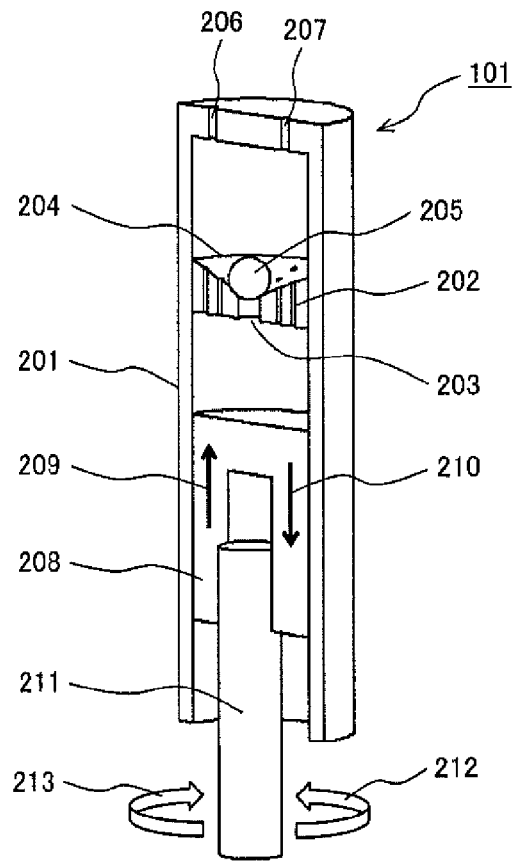
FIG. 9 is a longitudinal sectional view of a fluid device configuring the oil content measurement device shown in FIG. 1.
Figure 10:
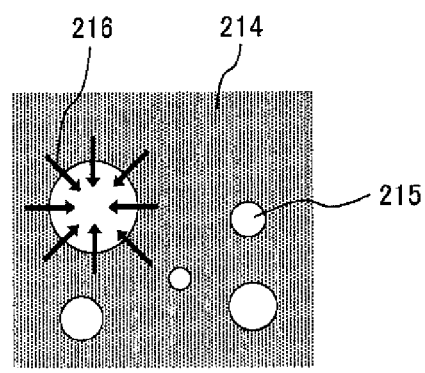
FIG. 10 is an explanatory drawing of a principle with which the oil content in the water to be treated penetrates and is extracted into hexane.
Figure 11:
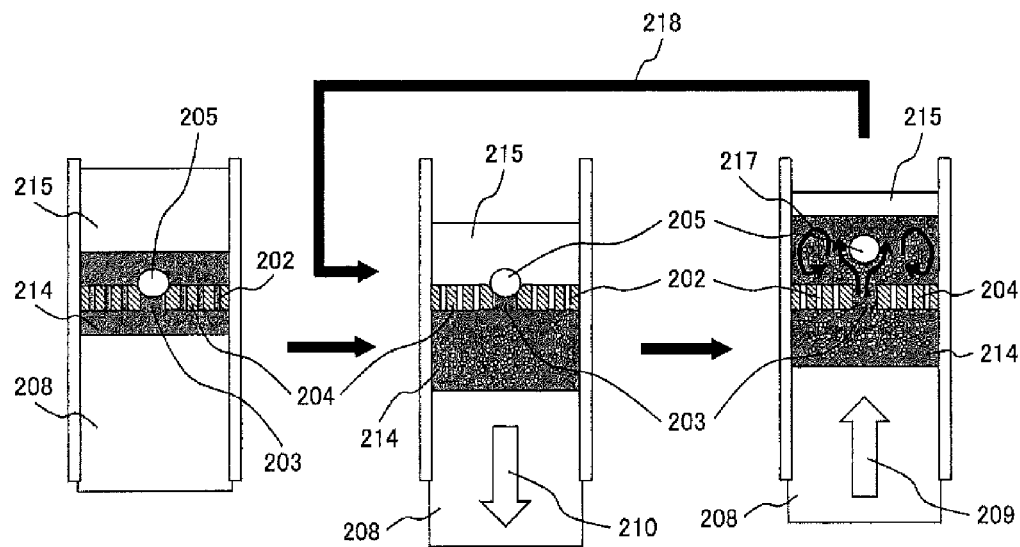
FIG. 11 is an explanatory drawing of an operation sequence of the fluid device shown in FIG. 9.

Next, an inner structure, operation, and functions of the fluid device 101 will be described with reference to FIGS. 9 through 11. FIG. 9 is a longitudinal sectional view of the fluid device 101 configuring the oil content measurement device 1 shown in FIG. 1, FIG. 10 is an explanatory drawing of a principle with which the oil content in the water to be treated penetrates and is extracted into hexane, and FIG. 11 is an explanatory drawing of an operation sequence of the fluid device 101.

As shown in FIG. 9, the fluid device 101 is composed of a syringe 201 of a substantially cylindrical shape in outer view, a piston 208 which moves upward and downward in the syringe 201, and a piston rod 211 which moves the piston 208 directly upward and downward by a driving force from the motor 102 coupled to the piston 208. Also provided inside the syringe 201 is a partition part 204 which vertically divides an inner space of the syringe 201 into two chambers along a longitudinal direction. As shown in FIG. 9, a top surface of the partition part 204 is formed of a columnar member having a conical recess which is located in substantially center thereof, and the partition part 204 comprises a communicating hole 203 (hereinafter referred to as communicating hole) as a first through hole which penetrates along the longitudinal direction of the syringe 201, and a plurality of small-diameter nozzles 202 (hereinafter referred to as small-diameter nozzles) as second through holes which are formed around the communicating hole 203 and which penetrate along the longitudinal direction of the syringe 201. A hole diameter of the communicating hole 203 is larger than that of the small-diameter nozzle 202, and the communicating hole 203 is provided with a spherical body 205 having a sufficiently large diameter to close the communicating hole 203. In the present embodiment, the spherical body is used as the one which closes the communicating hole 203, but a conical body may be used, or a member may be disposed which has a check valve function of preventing a flow from the upper chamber to the lower chamber through the communicating hole 203 with the partition part 204 as a boundary.

Moreover, formed on a top surface of the syringe 201 are an inflow port 206 and an outflow port 207 which can be respectively connected to the flow-in pipe 106 and the flow-out pipe 107. The suction of the hexane and the water to be treated from the flow-in port 206 through the flow-in pipe 106 and the discharge of the hexane after the oil content extraction from the flow-out port 207 to the flow-out pipe 107 are realized by downward movement of the piston 208 in a direction of an arrow 210 and upward movement thereof in a direction of an arrow 209. Formed at a central part of the piston 208 is a female screw (not shown), which is coupled through a screw thread (not shown) formed at the piston rod 211. Further, the piston rod 211 is coupled to the motor 102 shown in FIG. 1, and rotation of the motor 102 turns the piston rod 211, whose rotational displacement is converted into upward or downward linear displacement of the piston 208.

Although not shown, in order to perform such conversion from the rotational displacement into the linear displacement, a mechanism of constraining the rotational displacement is provided so that the piston 208 is not turned following the rotation of the piston rod 211. With a design based on normal screw standards, the piston 208 moves down in the direction of the arrow 210 when the piston rod 211 rotates in a right-handed rotation direction 212 in FIG. 9, and moves upward in the direction of the arrow 209 when the piston rod 211 rotates in a left-handed rotation direction 213.

Moreover, adjustment of lifting power in the direction of the arrow 209 applied to the piston rod 211 is made by adjusting, for example, a driving voltage, current, or a number of pulses of the motor 102 shown in FIG. 1 and then controlling a torque generated by a rotation axis of the motor 102 by the controller 105. Used as the motor 102 here is, for example, a stepping motor.

Next, how the oil content is extracted from the water to be treated into the hexane in the fluid device 101 will be described. As typical characteristics of the hexane as the solvent, the oil is dissolved but is not mixed with water due to its hydrophobic property. To measure the oil content in accordance with the aforementioned official law, while the water to be treated and the hexane are put in a container and oscillated, the oil content on water to be treated side is extracted into the hexane. Upon this extraction, the hexane 215 is dispersed in fine liquid droplets in the water to be treated 214 as shown in FIG. 10. In this state in which the hexane 215 is dispersed, a total area of a boundary surface between the water to be treated 214 and the hexane 215 increases, and as shown in FIG. 10, the oil content 216 on the water to be treated side efficiently moves towards the hexane 215 via the boundary surface as shown by arrows.

The present embodiment is characterized by forming the dispersed state of the hexane 215 as in FIG. 9 by fluidical operation using the nozzle instead of oscillating the water to be treated 214 and the hexane 215 with the whole container. As shown in FIG. 10, upon fluid passage through a narrow flow path like the small-diameter nozzle 202 at a fast flow speed, a jet flow is generated at an outlet of the small-diameter nozzle 202. At a flow filed inside the jet flow, strong sheer stress is generated, and thus near the outlet of the small-diameter nozzle 202, one of two phase liquids (the water to be treated 214 and the hexane 215 in the present embodiment) is repeatedly split, and is further split into fine liquid droplets. Using such two-phase fluid characteristics, a state in which the fine liquid droplets of the hexane 215 are dispersed in the water to be treated 214 is provided, enhancing the extraction of the oil content in the water to be treated 214 into the phase of the hexane 215.

When the piston 208 is in a stopped state as shown in a left view of FIG. 11, the hexane 215 and the water to be treated 214 are separated from each other. This is because the hexane 215 has lower density than the water to be treated 214 and the hexane 215 is constantly located on a top side in the state in which the both are separated from each other. Promptly moving the piston 208 downward as shown in a middle view of FIG. 11 results in closing of the communicating hole 203 by the hexane 215 and the flow paths communicating from the upper chamber to the lower chamber with the partition part 204 as the boundary are only the plurality of small-diameter nozzles 202. At this point, moving the piston 208 downward at a sufficient speed results in formation of a jet flow near an outlet of each of the small-diameter nozzles 202, and upon passage of the phase of the hexane 215 through this small-diameter nozzle 202, it is dispersed in fine liquid droplets in the phase of the water to be treated 214. The dispersion of the phase of the hexane 215 into the phase of the water to be treated 214 in this manner can increase the total area of the boundary surface between the both, which promotes the oil content extraction by the hexane.

Next, in this dispersed state, moving the piston 208 upward at a slow speed that causes slight floating of the spherical body 205 as in a right view of FIG. 11 results in formation of a flow shown by arrows 217 in the upper chamber by a liquid containing the hexane which is in the dispersed state or to which the oil content has been extracted, and causes movement to the upper chamber while mixing the liquid droplets of the hexane 215 and the water to be treated 214. This mixture makes concentration of the oil content of the hexane near the boundary surface uniform, which further enhances the oil content movement into the hexane.

In the process of extracting the oil content into the hexane (hereinafter referred to as solvent extraction process), which process corresponds to the preliminary treatment of the water to be treated 214 in the oil content measurement device 1 of the present embodiment, as shown in the middle and right views of FIG. 11, the downward movement 208 and upward movement 209 of the piston 208 are repeatedly 218 executed. This consequently increases the area of the boundary surface between the water to be treated 214 and the hexane 215 and the mixture of the both phases is performed, which can achieve the extraction without oscillating the whole container. This increase in the total area of the boundary surface and the mixture of the dispersed liquid are repeated until the oil content almost completely moves towards the hexane 215.

At a state at which the oil content 216 in the water to be treated 214 has been almost completely extracted into the phase of the hexane 215, the piston 208 is once put into a stopped state, and is put in place as shown in the left view of FIG. 11, turning the both into a dispersed state again. Then while the flow-in port 206 is closed by a control valve, a pinch valve, or the like, not shown, and a predetermined amount of hexane 215 after the oil content extraction is fed to the sensor unit 103 by the dispensing nozzle 108 through the flow-out port 207 and the flow-out pipe 107 shown in FIG. 1 while moving the piston 208 upwards at a slow speed (moving it in a continuously dispersed state).

Figure 12:
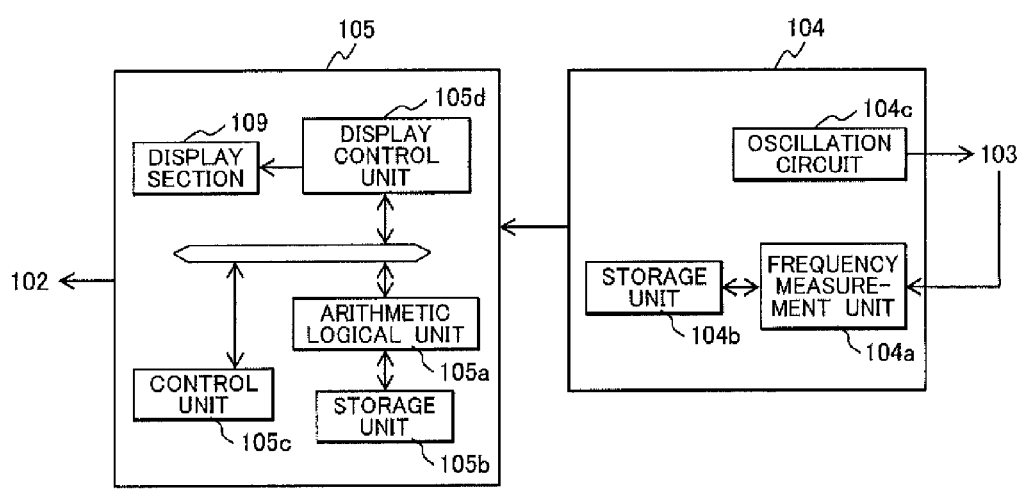
FIG. 12 is a functional block diagram of a sensor circuit and a controller shown in FIG. 1.

Here, configuration of the sensor circuit 104 and the controller 105 shown in FIG. 1 will be described. FIG. 12 shows a functional block diagram of the sensor circuit 104 and the controller 105. The sensor circuit 104 comprises an oscillation circuit 104*c* for oscillating the quartz crystal oscillator 33 in the sensor unit 103 with the fundamental resonance frequency $f_0$, a frequency measurement unit 104*a* which measures, with a predetermined period, the resonance frequency of the quartz crystal oscillator 33 after the feeding of the predetermined amount of hexane, into which the oil content in the water to be treated has been extracted, to the region of the quartz crystal oscillator 33 water-tightly sealed at the upper O ring 36 via the opening part 39 defined by the top surface of the upper casing 34, and a storage unit 104*b*. Here, the period with which the resonance frequency of the quartz crystal oscillator 33 is measured is set at, for example, 0.1 sec. Moreover, the controller 105 comprises an arithmetic logical unit 105*a* which executes reading of various programs previously stored in a storage unit 105*b*, a control unit 105*c* which adjusts, for example, the driving voltage, current, or number of pulses of the motor 102 shown in FIG. 1 to control the torque generated at the rotary axis of the motor 102, and a display control unit 105*d* for displaying, at the display unit 109, results of the calculation performed by the arithmetic logical unit 105*a*, namely, the concentration of the oil content in the water to be treated above-described. Note that the arithmetic logical unit 105*a* and the control unit 105*c* may be implemented integrally. Moreover, the control unit 105*c* performs, in addition to control of the motor 102 above-described, control of operation timing of the oscillation circuit 104*c* in the sensor circuit 104, control of operation of positioning the dispensing nozzle 108 with respect to the sensor unit 103, discharging the hexane after the oil extraction to the quartz crystal oscillator 33 water-tightly sealed by the upper O ring 36 from the dispensing nozzle 108, and sucking, with the dispensing nozzle 108, the hexane after the oil content extraction fed to the quartz crystal oscillator 33 water-tightly sealed by the upper O ring 36, and the like. Here, the control of the motor 102 as the stepping motor includes outputting of the number of pulses upon the discharge of the hexane after the oil content extraction by the dispensing nozzle 108 and the number of pulses upon the suction of the supplied hexane after the oil content extraction by the dispensing nozzle 108. Moreover, the storage unit 105*b* previously stores the distance h1 between the tip part of the dispensing nozzle 108 and the quartz crystal oscillator 33 above-mentioned.

Next, after the extraction of the oil content in the water to be treated into the hexane as the solvent (solvent extraction process) by the aforementioned fluid device 101, the supply of the hexane after the oil content extraction to the sensor unit 103 and the measurement by the quartz crystal oscillator 33 forming the sensor unit 103 will be described. FIGS. 13 to 16 are explanatory drawing expressing states of the oil content measurement process after the solvent extraction process. Illustrated in particular in FIGS. 13 to 16 are states of the dispensing nozzle 108 and the sensor unit 103.

Figure 13:
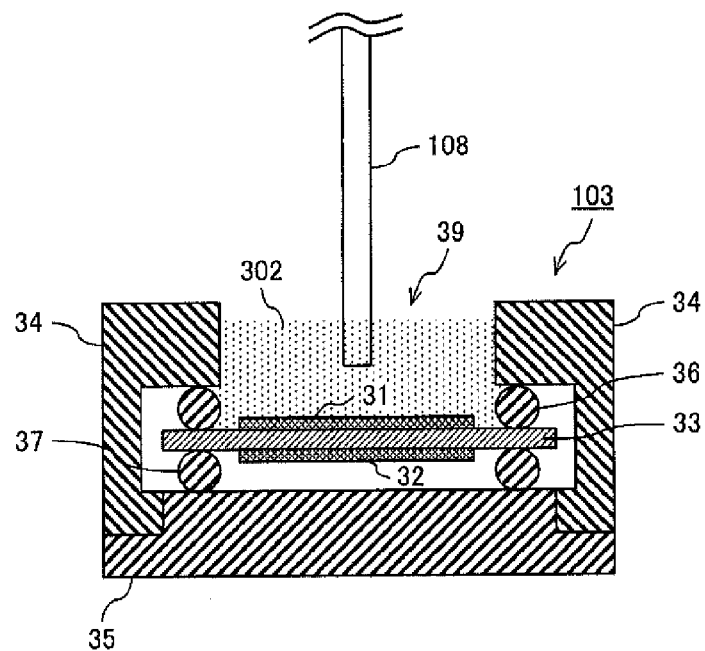
FIG. 13 is an explanatory drawing expressing a state of an oil content measuring step after the solvent extracting step.

First, as shown in FIG. 13, as described above, the dispensing nozzle 108 is positioned with respect to the sensor unit 103 so as to reach the distance h1 between the tip part of the dispensing nozzle 108 and the quartz crystal oscillator 33. Then by the motor 102 as the stepping motor, the piston 208 is moved upward at a slow speed in correspondence with a predetermined number of pulses, whereby hexane 302 after the oil content extraction is discharged to the sensor unit 103 by the dispensing nozzle 108 via the flow-out port 207 and the flow-out pipe 107 of the fluid device 101. This discharge of the hexane 302 after the oil content extraction by this dispensing nozzle 108 is executed until the tip part of the dispensing nozzle 108 is immersed in the hexane 302 after the oil content extraction. As a result, as shown in FIG. 13, the hexane 302 after the oil content extraction is fed to the region of the quartz crystal oscillator 33 water-tightly sealed by the upper O ring 36, and its liquid surface reaches up to an area near a top part in the opening part 39 defined by the top surface of the upper casing 34.

Figure 14:
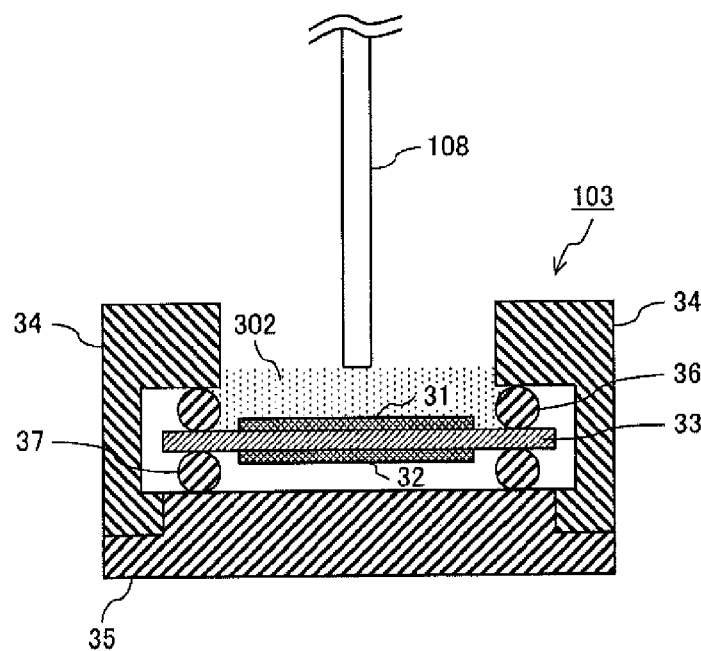
FIG. 14 is an explanatory drawing expressing a state of the oil content measuring step after the solvent extracting step.

By the motor 102, the piston 208 is moved downward at a slow speed in correspondence with a predetermined number of pulses, and the hexane 302 after the oil content extraction in the sensor unit 103 is sucked by the dispensing nozzle 108. The sucked hexane 302 after the oil content extraction inversely flows in the flow-out pipe 107 and is delivered back into the fluid device 101 from the flow-out port 207. Continuing operation of the suction by the dispensing nozzle 108 results in a gradual decrease in the liquid surface of the hexane 302 after the oil content extraction in the sensor unit 103, and finally reaches an empty suction state. At a time point at which the empty suction state has been reached, the suction of the hexane 302 after the oil content extraction by the dispensing nozzle 108 is automatically stopped, and the tip part of the dispensing nozzle 108 immersed in the hexane 302 after the oil content extraction up to this point is separated from the hexane 302 after the oil content extraction. As a result of this, as shown in FIG. 14, the liquid surface of the hexane 302 after the oil content extraction decreases to a height of the liquid surface corresponding to a position of the tip part of the dispensing nozzle 108. This results in supply of a constant amount of the hexane 302 after the oil content extraction to the sensor unit 103. Here, the constant amount of the fed hexane 302 after the oil content extraction, as above-described, becomes a volume based on the distance h1 between the tip part of the dispensing nozzle 108 and the quartz crystal oscillator 33 and the area of the region of the quartz crystal oscillator 33 water-tightly sealed by the upper O ring 36 (the area of the surface electrode 31).

Figure 15:
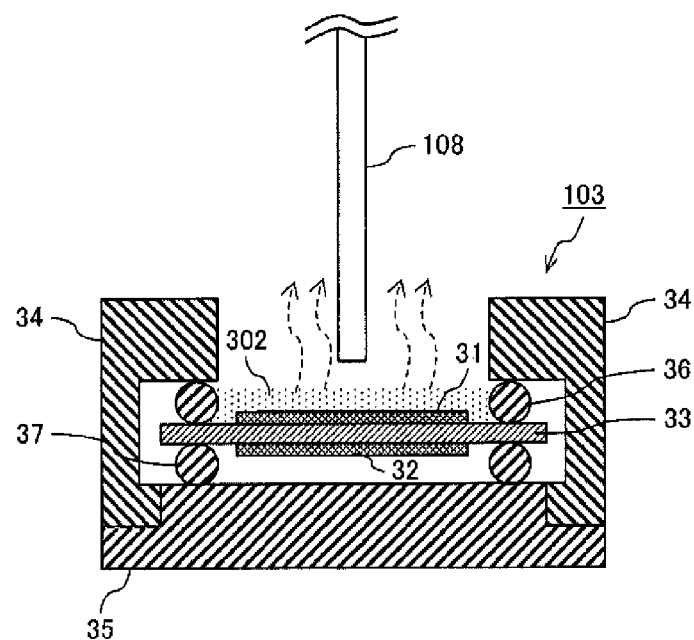
FIG. 15 is an explanatory drawing expressing a state of the oil content measuring step after the solvent extracting step.
Figure 16:
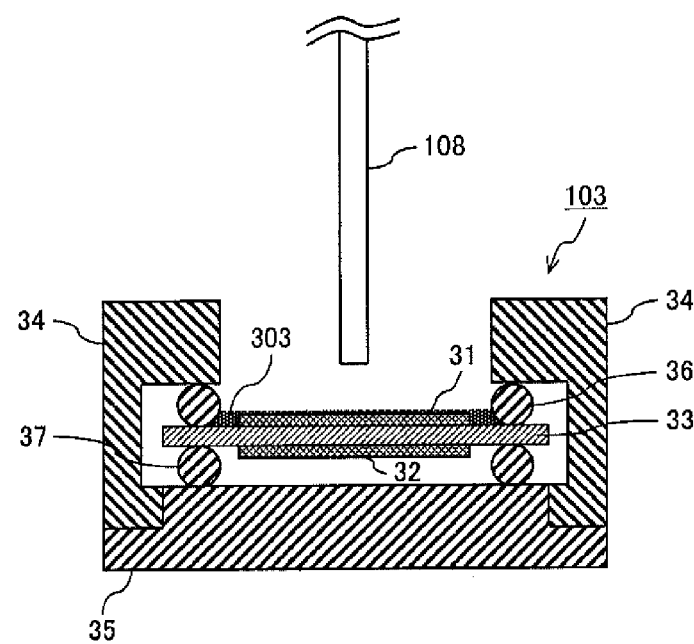
FIG. 16 is an explanatory drawing expressing a state of the oil content measuring step after the solvent extracting step.

With time passage from the state shown in FIG. 14, of the hexane 302 after the oil content extraction, only the highly volatile hexane is evaporated. As shown in FIG. 15, the hexane evaporation further reduces the liquid surface of the hexane 302 after the oil content extraction in the sensor unit 103. Then after complete hexane evaporation, only the oil content extracted into the hexane, that is, as shown in FIG. 16, only oil content 303 after the solvent evaporation deposits and remains on the quartz crystal oscillator 33 and the surface electrode 31 formed on the top surface of the quartz crystal oscillator 33. Before discharge of the hexane after the oil content extraction from the dispensing nozzle 108 shown in FIG. 13 to the sensor unit 103, the frequency measurement unit 104a (FIG. 12) configuring the sensor circuit 104 measures the resonance frequency of the quartz crystal oscillator 33 with, for example, a period of 0.1 sec.

Figure 17:
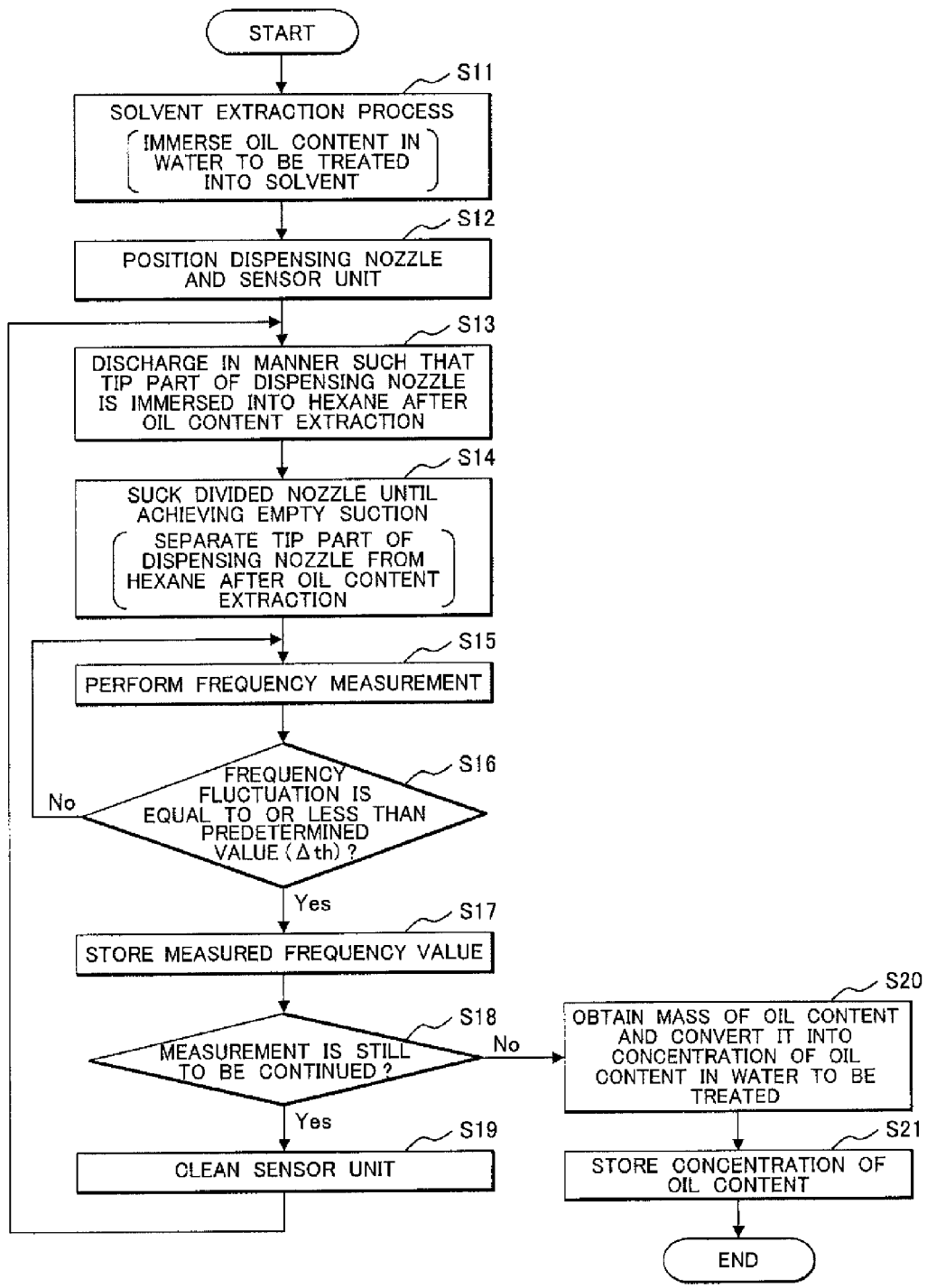
FIG. 17 is a flow diagram of overall processing by the oil content measurement device in relation with an embodiment of the present invention.
Figure 18:
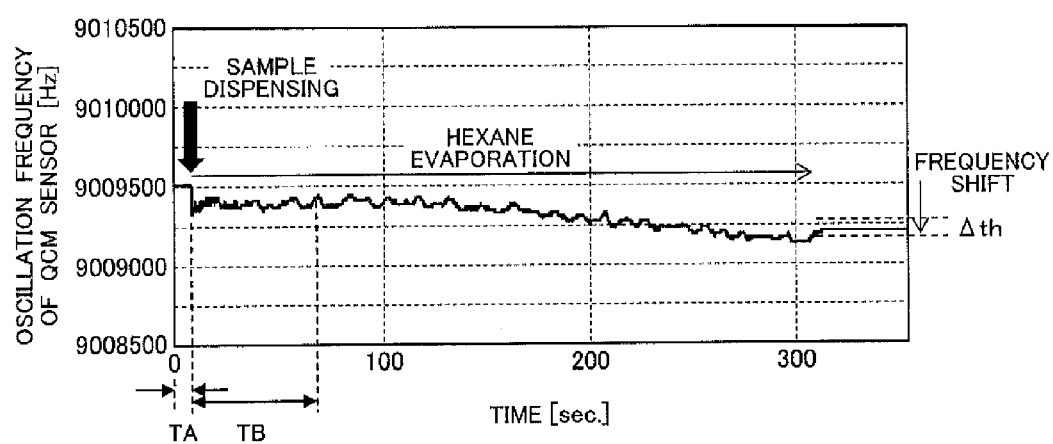
FIG. 18 is a diagram showing a temporal change of a resonance frequency measured by the oil content measurement device shown in FIG. 1.

FIG. 17 shows a flow of overall processing of the oil content measurement device 1 executed by these sensor circuit 104 and controller 105. Moreover, FIG. 18 shows a temporal change of the resonance frequency measured by the oil content measurement device 1. As shown in FIG. 17, after the solvent extraction process (step S11) in which the fluid device 101 described in FIGS. 9 through 11 above is operated to move and extract the oil content in the water to be treated into the hexane as the solvent, the dispensing nozzle 108 and the sensor unit 103 are positioned (step S12). In step S12, the control unit 105c configuring the controller 105 reads the distance h1 between the tip part of the dispensing nozzle 108 and the quartz crystal oscillator 33 which distance is stored in the storage unit 105b. Based on the read distance h1, the control unit 105c drives, in a z-direction, a positioning mechanism, not shown, which is provided in the dispensing nozzle 108, whereby the tip part of the dispensing nozzle 108 is positioned at a location above the quartz crystal oscillator 33 away therefrom by the distance h1. Here, the positioning mechanism, not shown, may be so configured as to move the sensor unit 103 in the z-direction instead of being so configured as to move the dispensing nozzle 108 in the z-direction. That is, the positioning mechanism may be in any mode as long as it is so configured as to be capable of moving the dispensing nozzle 108 and the sensor unit 103 relatively to each other in the z-direction. Moreover, a direction of the movement is not limited to the z-direction, and thus it may be x- or y-directions, and in any case, the positioning mechanism may be so configured as to be capable of moving the dispensing nozzle 108 and the sensor unit 103 relatively to each other.

In step S13, in order that the hexane 302 after the oil content extraction which hexane has been fed from the dispensing nozzle 108 to the sensor unit 103 reaches the predetermined amount (an amount of the tip part of the dispensing nozzle 108 immersed in the hexane 302 after the oil content extraction), the control unit 105c of the controller 105 adjusts, for example, the driving voltage or the number of pulses of the motor 102, and moves the piston 208 in the fluid device 101 upward at a slow speed. Moreover, before start of the operation of this step S13, the quartz crystal oscillator 33 is previously put into a resonant state by the oscillation circuit 104c in the sensor circuit 104, and a resonance frequency at this point is defined as the fundamental resonance frequency $f_0$ and stored into the storage unit 104b and the storage unit 105b. Upon end of step S13, the state shown in FIG. 13 described above is reached.

Next, in step S14, in a manner such as to suck, by the dispensing nozzle 108, the hexane 302 after the oil content extraction which hexane has been fed into the sensor unit 103, the control unit 105c of the controller 105 adjusts, for example, the driving voltage or the number of pulses of the motor 102, and moves the piston 208 in the fluid device 101 downward at a slow speed. As a result, the hexane 302 after the oil content extraction in the sensor unit 103 reversely flows into the flow-out pipe 107 and is delivered back to the fluid device 101 from the flow-out port 207, and the liquid surface of the hexane 302 after the oil content extraction in the sensor unit 103 gradually declines. The tip part of the dispensing nozzle 108 separates from the hexane 302 after the oil content extraction, turning into an empty suction state, and the operation of sucking the hexane 302 after the oil content extraction by the dispensing nozzle 108 stops. Upon end of step S14, the state shown in FIG. 14 described above is reached.

Next, in step S14, the resonance frequency of the quartz crystal oscillator 33 in a state in which the liquid surface of the hexane 302 after the oil content extraction in the sensor unit 103 is located at the position corresponding to the tip part of the dispensing nozzle 108 as shown in FIG. 14 is measured with a predetermined period (for example, 0.1 sec) at the frequency measurement unit 104a in the sensor circuit 104 (step S15). As a result, a fluctuation in the resonance frequency of the quartz crystal oscillator 33 which changes with time (every measurement period) is obtained. This fluctuation in the resonance frequency is attributable to the evaporation of the hexane as the solvent described in FIG. 15.

A threshold value (Δth) of the fluctuation in the resonance frequency is previously stored in the storage unit 104b in the sensor circuit 104, and the frequency measurement unit 104a judges whether or not a difference between the current resonance frequency measured in step S15 and a previous value (resonance frequency measured with the last measurement period) is equal to or less than a predetermined value (the threshold value Δth) (step S16). In step S16, if the fluctuation in the resonance frequency is larger than the predetermined value (threshold value Δth), the processing returns to step S15, where the resonance frequency with a next measurement period is measured. In contrast, if it is judged as a result of the judgment in step S16 that the fluctuation in the resonance frequency is equal to or less than the predetermined value (threshold value Δth), the processing proceeds to step S17. The comparison of the fluctuation in the resonance frequency with the predetermined value (threshold value Δth) in step S16 is focused on a fact that, after the complete hexane evaporation from the hexane 302 after the oil content extraction on the quartz crystal oscillator 33 and the surface electrode 31 formed on the top surface of the quartz crystal oscillator 33, only the oil content 303 after the solvent evaporation deposits on the quartz crystal oscillator 33 and the surface electrode 31, as described in FIG. 16, and the fluctuation in the resonance frequency measured with each period thereafter is none excluding a fluctuation caused by disturbance.

In step S17, the resonance frequency judged to be equal to or less than the predetermined value in step S16 is stored into the storage unit 104b in the sensor circuit 104. The resonance frequency stored in the storage unit 104b at this point is transmitted to the controller 105 and stored into the storage unit 105b in the controller 105.

Subsequently, it is judged whether or not to continue the measurement (step S18). The judgment on whether or not to continue the measurement is in accordance with a schedule of measurement of oil content in water to be treated which schedule is previously stored in the storage unit 105b in the controller 105. If it is judged in step S18 that the measurement is to be continued, the processing proceeds to step S19 to clean the sensor unit 103, and returns to step S13 and repeatedly executes steps thereafter. The cleaning of the sensor unit 103 in step S19 is realized by, for example, dropping pure hexane into the sensor unit 103 and thereby melting the oil content 303 after the solvent evaporation, which deposits on the quartz crystal oscillator 33 and the surface electrode 31, and then blowing off the hexane containing the oil content 303 after the solvent evaporation by an air duster or the like. Judgement on whether or not the cleaning of the sensor unit 103 has been favorably executed in step S19 can easily be confirmed by, for example, measuring the resonance frequency of the quartz crystal oscillator 33 in the sensor unit 103 after the cleaning and then making comparison by the frequency measurement unit 104a of the sensor circuit 104 between the resonance frequency after the cleaning and the fundamental resonance frequency $f_0$ stored in the storage unit 104b described above.

In contrast, if it is judged in step S18 that the measurement is not to be continued, the processing proceeds to step S20. In step S20, the arithmetic logical unit 105a in the controller 105, based on the formula (1) described above, obtains mass (m) of the oil content (oil content 303 after the solvent evaporation) as the remaining deposit on the surface electrode 31. In step S14, based on a volume (V1) of the hexane 302 after the oil content extraction in the sensor unit 103 when the liquid surface of the hexane 302 after the oil content extraction is located at the tip part of the dispensing nozzle 108 and the obtained mass of oil content, concentration of the oil content in the hexane 302 after the oil content extraction is calculated. Moreover, in step S11, based on a volume (V2) of the water to be treated containing the oil content introduced into the fluid device 101 through the flow-in pipe 106, a volume (V3) of the hexane similarly introduced into the fluid device 101 through the flow-in pipe 106, and the obtained mass (m) of oil content, concentration of the oil content in the water to be treated is obtained. Namely, the obtained mass (m) of the oil content is converted into the concentration of the oil content in the water to be treated (step S20). The volume (V2) of the water to be treated containing the oil content described above and the volume (V3) of the hexane described above are already known. The concentration of the oil content in the water to be treated which has been obtained in step S20 is stored into the storage unit 105b (step S21), and the processing ends.

FIG. 18 shows the temporal change of the resonance frequency measured by the oil content measurement device 1 of the present embodiment. FIG. 18 shows the temporal change of the resonance frequency measured by the sensor circuit 104 where time is plotted at a horizontal axis and the resonance frequency of the quartz crystal oscillator 33 of the sensor unit 103 as the QCM sensor is plotted at a vertical axis.

Defined in FIG. 18 is that the distance h1 between the tip part of the dispensing nozzle 108 and the quartz crystal oscillator 33 is 0.50 mm, the outer diameter (diameter) D1 of the surface electrode 31 and the back electrode 32 is 5.0 mm, the inner diameter D2 of the upper O ring 36 and the lower O ring 37 is 5.5 mm, the aperture diameter W1 of the opening part 39 is 5.5 mm, and the outer diameter D3 of the disk-like quartz crystal oscillator 33 is 8.7 mm.

As described in FIG. 17, before the start of the feeding of the hexane 302 after the oil content extraction from the dispensing nozzle 108 to the sensor unit 103, the frequency measurement unit 104a of the sensor circuit 104 measures the resonance frequency of the quartz crystal oscillator 33 with a predetermined measurement period (0.1 sec), and stores it into the storage unit 104b. As shown in FIG. 18, a term TA is a discharge term, that is, a term between a term before execution of step S12 shown in FIG. 17 or before execution of step S13 after the execution of step S12 and a term after the execution of step S13. In the term TA, upon start of step 13 described above, the hexane 302 after the oil content extraction is fed to a top of the sensor unit 103 by the tip part of the dispensing nozzle 108 (the state shown in FIG. 13). As a result, the measured resonance frequency abruptly decreases.

A term TB is a suction term, i.e., a term in which step S14 shown in FIG. 17 is executed. In the term TB, as described above, the piston 208 of the fluid device 101 moves downward at a slow speed, whereby the liquid surface of the hexane 302 after the oil content extraction in the sensor unit 103 gradually declines, and at an ending time point of the term TB, the liquid surface of the hexane 302 after the oil content extraction in the sensor unit 103 comes to a height corresponding to the position of the tip part of the dispensing nozzle 108 (the state shown in FIG. 14). Then the amount of the fed hexane 302 after the oil content extraction in the sensor unit 103 was 14.2 μL shown in Table 1 described above. In the term TB, the measured resonance frequency increases while fluctuating in comparison to that in the term TA. From a time point at which step S13 described above starts (expressed as sample dispensing in FIG. 18), the hexane in the hexane 302 after the oil content extraction is highly volatile and thus is continuously evaporated (the state shown in FIG. 15). In FIG. 18, a width of the fluctuation of the resonance frequency measured decreases from a time point at which 300 seconds has passed, and becomes equal to or less than the predetermined value (threshold value Δth) in step S16 shown in FIG. 17 (the state shown in FIG. 16). As a result, the mass (m) of the oil content contained in the hexane 302 after the oil content extraction can be obtained.

In comparison to a method of dropping, from the dispensing nozzle, a minute amount (less than several microliters) of the hexane after the oil content extraction on the surface electrode, in the present embodiment, the amount of the hexane 302 after the oil content extraction which hexane 302 is fed into the sensor unit 103 increases, and thus it takes time for the measured resonance frequency of the quartz crystal oscillator 33 to reach the predetermined value (threshold value Δth), as shown in FIG. 18. However, in the present embodiment, at one trial of measurement, the amount of hexane after the oil content extraction which hexane is fed to the sensor unit 103 can be increased to accurately and reliably measure the concentration of the oil content contained in the produced water as the water to be treated through one trial of measurement, for example, even in a case where oil content in the produced water or the like is dilute.

It is configured in the present embodiment that the resonance frequency judged to be equal to or less than the predetermined value in step S16 is stored into the storage unit 104b and the storage unit 105b, although not limited thereto, and the resonance frequency measured with the predetermined period may be stored into the storage unit 104b and the storage unit 105b on an individual case basis. In this case, it is possible to display relationship between the measured resonance frequency and measurement time at the display unit 109 by the display control unit 105d. Moreover, the judgment in step S16 may be executed by the arithmetic logical unit 105a instead of the frequency measurement unit 104a.

The flow shown in FIG. 17 is executed by control by the controller 105, which can therefore make it possible to automate the oil content measurement device 1.

According to the present embodiment, even in a case where the oil content remaining in the water to be treated at the water treatment site is dilute, this oil content can accurately be measured through one trial of measurement.

Moreover, according to the present embodiment, the oil content in the water to be treated can effectively be moved into the hexane as the solvent, and the hexane after the subsequent oil content extraction can be used for measuring the concentration of the oil content by the QCM method.

Moreover, it is possible to automate the measurement of the concentration of the oil content, which also makes it possible to perform the measurement of the concentration of the oil content by a developer at the Oil & Gas water treatment site without requesting a test technician in an analysis chamber for the measurement as in a conventional case. Moreover, since oscillation is not utilized for the oil content extraction into the hexane, which can therefore avoid any trouble caused by the oscillation.

In the present embodiment, the hexane is used as an oil content extracting solvent which is adopted in the Japanese official law (Water Pollution Control Law), but the solvent is not limited to this and any solvent, for example, acetone or dichloromethane, which can have the same functions and provide the same effect can be used.

The present invention is not limited to the embodiment described above, and includes various modified embodiments. For example, the embodiment above has been described in detail for easier understanding of the present invention, but the present invention is not necessarily limited to the one provided with all the configuration described above.

REFERENCE SIGNS LIST

1 Oil Content Measurement Device
31 Surface Electrode
32 Back Electrode
33 Quartz crystal Oscillator
34 Upper Casing
35 Lower Casing
36 Upper O ring
37 Lower O ring
38 Jig
39 Opening part
101 Fluid device
102 Motor
103 Sensor unit
104 Sensor circuit
104a Frequency measurement unit
104b Storage unit
104c Oscillation circuit
105 Controller
105a Arithmetic Logical unit
105b Storage unit
105c Control unit
105d Display control unit
106 Flow-in pipe
107 Flow-out pipe
108 Dispensing nozzle
109 Display unit
110 Water to be treated and hexane
201 Syringe
202 Small-diameter nozzle
203 Communicating hole
204 Partition part
205 Spherical body
206 Flow-in port
207 Flow-out port
208 Piston
211 Piston rod
214 Water to be treated
215 Hexane
216 Oil content in water to be treated
301 Deposit
302 Hexane after oil content extraction
303 Oil content after solvent evaporation

What is claimed is:
1. An oil measurement device comprising:
a fluid device which mixes water to be treated containing oil content with solvent and extracts the oil content into the solvent;

a sensor unit which includes a casing storing a quartz crystal oscillator therein with a ring-like spacer in between;

a dispensing nozzle connected to the fluid device, being disposed above the quartz crystal oscillator of the sensor unit at a predetermined gap therebetween, which feeds a predetermined amount of the solvent after the oil content has been extracted thereinto onto the quartz crystal oscillator;

a sensor circuit which measures a resonance frequency of the quartz crystal oscillator with a predetermined period;

a controller which controls at least the fluid device and the sensor circuit; and an arithmetic logical unit which receives the resonance frequency of the quartz crystal oscillator in the sensor unit to which the predetermined amount of the solvent after the oil content has been extracted thereinto has been fed by the dispensing nozzle from the sensor circuit, and measures the oil content remaining on the quartz crystal oscillator after the solvent has evaporated based on a change amount of the received resonance frequency.

2. The oil content measurement device according to claim 1, wherein the sensor unit further comprising:
a surface electrode and a back electrode respectively formed on a front surface and a back surface of the quartz crystal oscillator;
an upper ring-like spacer which is disposed on a top surface of the quartz crystal oscillator and on an outer circumference side of the surface electrode; and
a lower ring-like spacer which is disposed on a bottom surface of the quartz crystal oscillator and an outer circumference side of the back surface electrode.

3. The oil content measurement device according to claim 2, wherein the casing further comprising:
an upper casing which has an opening part penetrating towards the quartz crystal oscillator stored therein; and
a lower casing which engages with the upper casing and forms, with the upper casing, an inner space storing the quartz crystal oscillator,
wherein a top surface of the upper ring-like spacer abuts against a bottom surface of the upper casing defining the opening part, and a bottom surface of the lower ring-like spacer is positioned in a manner such as to abut against a top surface of the lower casing and be pressed.

4. The oil content measurement device according to claim 3, wherein the controller makes control to perform suction operation of the dispensing nozzle until a tip part of the dispensing nozzle separates from a liquid surface of the solvent after the oil content has been extracted in the sensor unit after the solvent after the oil content extracted has been discharged by the dispensing nozzle so that the tip part of the dispensing nozzle is immersed in the solvent after the oil content extracted.

5. The oil content measurement device according to claim 4, wherein the upper casing has, on a bottom part of a side surface thereof, a convex part which protrudes from an outside to an inside and which defines a bottom part of the opening part, the lower casing has, at a substantially central part thereof, a columnar convex part pressing and fixing the lower ring-like spacer, and the upper casing is fixed through engagement between an outer circumferential surface of the columnar convex part provided at the lower casing and the side surface of the convex part defining the bottom part of the opening part.

6. The oil content measurement device according to claim 5, wherein an outer diameter of the columnar convex part provided at the lower casing is larger than an aperture diameter of the opening part defined by the top surface of the upper casing.

7. The oil content measurement device according to claims 3, wherein the controller includes a storage unit previously storing a vertical distance between the tip part of the dispensing nozzle and the quartz crystal oscillator when the tip part of the dispensing nozzle is located in the opening part of the upper casing, and
the controller positions the dispensing nozzle with respect to the sensor unit so as to achieve the vertical distance stored in the storage unit.

8. The oil content measurement device according to claim 7, wherein the opening part provided on the top surface of the upper casing is an aperture of a cylindrical shape, and
the top surface of the upper ring-like spacer abuts against the bottom surface of the upper casing defining the opening part, that is, surroundings of the opening part.

9. The oil content measurement device according to claim 8, wherein the fluid device further comprising:
a syringe of a substantially cylindrical shape which has therein a partition part having a plurality of holes and which has two spaces formed in a longitudinal direction by the partition part; and
a piston which is disposed inside of the syringe and below the partition part and is movable upward and downward in the syringe,
wherein through the upward and downward movement of the piston, the water to be treated containing the oil content and the solvent are made flow through the plurality of through holes in the syringe to thereby extract the oil content into the solvent.

10. The oil content measurement device according to claim 9, wherein the partition part having a columnar shape, further comprising:
a first through hole which penetrates through a substantially central part in horizontal cross section along a longitudinal direction of the syringe; and
a plurality of second through holes which are formed around the first through hole and penetrate along the longitudinal direction of the syringe,
wherein a hole diameter of the first through hole is larger than a hole diameter of the second through holes.

11. The oil content measurement device according to claim 10, wherein the controller moves the piston upward and downward a predetermined number of times, and makes the water to be treated containing the oil content and the solvent vertically flow through at least one of the first through hole and the second through holes.

12. The oil content measurement device according to claim 11,
wherein the controller stops the upward and downward movement of the piston to separate the solvent, into which the oil content has been extracted, from the water to be treated, and by moving the piston upward at a slow speed, supplies a predetermined amount of the solvent after the oil content extracted after the separation into the sensor unit through the dispensing nozzle.

13. The oil content measurement device according to claim 11,
wherein a surface of the partition part opposite to a surface facing the piston has a recess of a substantially conical shape,
a spherical body having a diameter larger than the hole diameter of the first through hole is disposed above the surface of the partition part having the recess of the conical shape, and
the first through hole is closed by the spherical body as a result of the downward movement of the piston by the controller.

14. The oil content measurement device according to claim 11,
wherein the solvent is dispersed in fine liquid droplets in the syringe as a result of upward and downward flow of the solvent through the second through holes.

15. The oil content measurement device according to claim 7,
wherein, under assumption that a difference between a resonance frequency, included in resonance frequencies with the predetermined period received by the sensor circuit, when a difference from a previous value becomes equal to or less than a predetermined value and a fundamental resonance frequency of the quartz crystal oscillator measured before the predetermined amount of the solvent after the oil content extracted is fed into the sensor unit is defined as a change amount of the resonance frequency, the arithmetic logical unit obtains mass of the oil content based on the change amount.

16. The oil content measurement device according to claim 15,
wherein the arithmetic logical unit, based on the obtained mass of the oil content and a volume of the water to be treated containing the oil content when the oil content is extracted into the solvent by the fluid device, obtains concentration of the oil content in the water to be treated containing the oil content.

* * * * *